United States Patent
Miyawaki et al.

(10) Patent No.: US 9,989,518 B2
(45) Date of Patent: Jun. 5, 2018

(54) METHOD FOR MEASURING AUTOPHAGY

(75) Inventors: Atsushi Miyawaki, Saitama (JP); Hiroyuki Katayama, Saitama (JP)

(73) Assignee: Japan Science and Technology Agency, Saitama (JP)

( * ) Notice: Subject to any disclaimer, the term of this patent is extended or adjusted under 35 U.S.C. 154(b) by 0 days. days.

(21) Appl. No.: 13/389,869

(22) PCT Filed: Oct. 8, 2010

(86) PCT No.: PCT/JP2010/063787
§ 371 (c)(1),
(2), (4) Date: Feb. 10, 2012

(87) PCT Pub. No.: WO2011/019082
PCT Pub. Date: Feb. 17, 2011

(65) Prior Publication Data
US 2012/0178119 A1    Jul. 12, 2012

(30) Foreign Application Priority Data

Aug. 10, 2009  (JP) ................................. 2009-185639

(51) Int. Cl.
*A61K 31/7088* (2006.01)
*G01N 33/50* (2006.01)
*G01N 21/64* (2006.01)
*G01N 21/80* (2006.01)

(52) U.S. Cl.
CPC ..... *G01N 33/5005* (2013.01); *G01N 21/6428* (2013.01); *G01N 33/5035* (2013.01); *G01N 21/80* (2013.01); *G01N 2021/6419* (2013.01); *G01N 2021/6421* (2013.01)

(58) Field of Classification Search
CPC ....... A61K 31/7088; G01N 2021/6419; G01N 21/6428; G01N 33/5005
USPC ......................................................... 435/29
See application file for complete search history.

(56) References Cited

U.S. PATENT DOCUMENTS

2009/0170073 A1    7/2009 Miyawaki et al.

FOREIGN PATENT DOCUMENTS

WO    WO-2004/111235 A1    12/2004

OTHER PUBLICATIONS

Rao et al. Fluorescence imaging in vivo: recent advances. Current Opinion in Biotechnology. 2007;18:17-25.*
Katayama et al. GFP-like proteins stably accumulate in lysosomes. Cell Structure and Function. 2008;33;1-12.*
Kogure et al. Fluorescence imaging using a fluorescent protein with a large Stokes shift. Methods. 2008;45:223-226.*
Kogure et al. A fluorescent variant of a protein from the stony coral Montipora facilitates dual-color single-laser fluorescence cross-correlation spectroscopy. Nature Biotechnology. 2006. 24(5):577-581.*
Riddle D. Feature article: how to make corals more colorful part 3—new information: red fluorescent pigments: DsRed-type. www.advancedaquarist.com. 2009;1-36.*
Carolos J. Rosado et al., "Rosella A fluorescent pH-biosensor for reporting vacuolar turnover of cytosol and organelles in yeast", Autophagy 4:2, 205-213, Feb. 16, 2008.
George T. Hanson et al., "Green Fluorescent Protein Variants as Ratiometric Dual Emission pH Sensors 1. Structural Characterization and Preliminary Application", Biochemistry 2002, 41, 15477-15488.
Hiroyuki Katayama et al., "Visualizing Autophagy With a pH-Sensitive GFP-Like Protein", Dai 82 Kai Annual Meeting of the Japanese Biochemical Society Program Koen Yoshishu, Sep. 25, 2009, 3T5p-1(3P-468).
International Search Report PCT/JP2010/063787 dated Aug. 26, 2010.
Lihong Zhang et al., "Small Molecule regulators of autophagy identified by an image-based high-throughput screen", PNAS, vol. 104, No. 48, Nov. 27, 2007, pp. 19023-19028.
Noboru Mizushima "Autophagy", Inflammation and Immunology, 2006, 14(4), pp. 569-571.
Katayama et al., "A Sensitive and Quantitative Technique for Detecting Autophage Events Based on Lysosomal Delivery," Chemistry & Biology, Aug. 26, 2011, 18:1042-1052.
EP Communication for PCT Application No. PCT/2010063787, Supplementary Search Report, dated Dec. 6, 2012, 3 pages.
Katayama et al., "A Sensitive and Quantitative Technique for Detecting Autophagic Events Based on Lysosomal Delivery," Chemistry & Biology, 2011, pp. 1042-1052, vol. 18, Elsevier Ltd.
Proikas-Cezanne et al., "A New Fluorescence-Based Assay for Autophagy," Chemistry & Biology, 2011, pp. 940-941, vol. 18, Elsevier Ltd.
Violot et al., "Reverse pH-Dependence of Chromophore Protonation Explains the Large Stokes Shift of the Red Fluorescent mKeima," Journal of American Chemical Society, 2009, pp. 10356-10357, vol. 131, The American Chemical Society.

* cited by examiner

*Primary Examiner* — Lynn Y Fan
(74) *Attorney, Agent, or Firm* — Foley & Lardner LLP

(57) ABSTRACT

This invention relates to a method for measuring autophagy in cells, comprising using, as a probe reagent, a single fluorescent protein, to measure a change in fluorescence properties of the fluorescent probe reagent depending on pH changes associated with autophagy, thereby determining the presence or activity of autophagy, wherein the single fluorescent protein is resistant to degrading enzyme activity in the lysosome or vacuole of the cell, it is not denatured or inactivated under acidic to neutral pH environment, and it is capable of changing excitation spectra or fluorescence spectra when located under the environments of acidic region and neutral region.

8 Claims, 3 Drawing Sheets
(2 of 3 Drawing Sheet(s) Filed in Color)

METHOD FOR MEASURING AUTOPHAGY

TECHNICAL FIELD

This invention relates to a method for measuring autophagy.

This invention also relates to a method of screening for therapeutic agents for a disease associated with autophagy anomalies using the method for measuring autophagy.

BACKGROUND ART

Autophagy is a pathway of degrading cytoplasmic materials ubiquitously observed in eucaryocytes. Autophagy is classified into three types based on its mechanisms; i.e., macroautophagy, microautophagy, and chaperone-mediated autophagy. In any pathway, cytoplasmic materials are ultimately translocated into lysosomes (vacuoles in the case of yeast or plants) and degraded by degrading enzymes existing therein. Examples of the cytoplasmic materials to be degraded include not only protein molecules but also organelles such as mitochondria and endoplasmic reticulum. Since autophagy is induced by nutrient starvation, supply of nutrient components to cells via recycling of the degraded cytoplasmic materials had been considered to be a main role thereof. However, autophagy has recently been found to be associated with various vital phenomena, such as quality control of proteins or organelles, bacterial infection, antigen presentation, cell death or apoptosis, and canceration. Since autophagy is associated with degradation and elimination of abnormal proteins that accumulate and aggregate in cells, it is suggested that autophagy is associated with neurodegenerative diseases such as Huntington's disease and Alzheimer's disease, which are considered to develop due to cell death or apoptosis caused by accumulation of abnormal proteins (Deretic, V. and Klionsky, D. J., Scientific American, Vol. 298, pp. 74-81, 2008). Under such circumstances, there are needs for developing a simple and accurate method for measuring autophagy with the aim of elucidating mechanisms of the vital phenomena or developing methods for treating diseases associated with such mechanisms.

In the past, autophagy had been measured by: observing cells under electron microscope; measuring an activity of an enzyme designed to be activated specifically upon degradation of a radioisotope-labeled protein or upon autophagy; or other techniques. However, such techniques required skills and times due to insufficient specificity for autophagy and complicated procedures.

In recent years, techniques for applying fluorescent proteins represented by GFP have been advanced, and techniques for labeling autophagy-associated proteins with a fluorescent protein and measuring their phamacokinetics by fluorescence methods such as microscopic imaging and flow cytometry has become generalized. Such techniques enabled simple measurement of autophagy in living cells.

In macroautophagy, a portion of cytoplasm is wrapped with a membrane called separation membrane at first, thereby forming a vesicle called autophagosome (having a diameter of about 1 μm). Then, the autophagosome is fused to a lysosome, whereby the incorporated cytoplasmic materials are then degraded. Among autophagy-related proteins that have heretofore been found, a protein related to autophagosome formation and localized in the membrane, such as LC3, is known. Thus, such protein is fused to a fluorescent protein and expressed in cells, and autophagy is mesured by monitoring the accumulation of the fusion protein in the vesicular structure or the decrease in fluorescence intensity caused by degradation in the lysosome (Mizushima, N., Int. J. Biochem. Cell Biol., Vol. 36, pp. 2491-2502, 2004; and Shvets, E. et al., Autophagy, Vol. 4, pp. 621-628, 2008).

However, because the formation of autophagosome is a phenominon observed only in the case of macroautophagy, it is impossible to detect microautophagy or chaperone-mediated autophagy by the method as mentioned above. In the case of microautophagy or chaperone-mediated autophagy, vesicles for transfer, such as autophagosome, are not formed, and cytoplasmic materials are thought to be directly incorporated into the lysosome. At present, however, research thereon has not advanced as that of macroautophagy, and there are no effective methods for measurement. It is thus impossible to determine the total amount of all types of autophagy occurring in cells.

While the pH in the cytoplasm is neutral (pH, around 7), the pH in the lysosome or vacuole in which cytoplasmic materials are degraded by autophagy is acidic (pH, around 4). There is a method that, through utilizing such pH properties, autophagy can be detected based on pH-dependent changes in fluorescent properties caused by transfer of a fluorescent probe reagent resistant to degrading enzymes to the lysosome or vacuole. Because the cytoplasmic materials are ultimately incorporated into the lysosome or vacuole in all types of autophagy, the total amount of autophagy can be measured by this method. For example, Rosado et al (Rosado, C. J. et al., Autophagy, Vol. 4, pp. 205-213, 2008) use a probe reagent prepared by ligating, via a linker peptide, a fluorescent protein (DsRed.T3) that emits fluorescence at a relatively constant level independent of pH changes in the environment, to a fluorescent protein (super ecliptic pHluorin) that exhibits lowered fluorescence intensity as pH becomes more acidic. DsRed.T3 is a fluorescent protein that emits red fluorescence (587 nm), and the super ecliptic pHluorin is a fluorescent protein that emits green fluorescence (508 nm). Such probe is expressed in the cytoplasm, pH changes that occur when the probe is incorporated into the lysosome together with other cytoplasmic materials are measured as changes in a ratio of intensities of two fluorescences having different colors, thereby determining the activity of autophagy.

Because Rosado et al employ two fluorescent proteins, there is a problem that their technique makes the accurate measurement of autophagy activities difficult for the following reasons: that because the size of a label becomes large, the activity or localization of the proteins may probably be inhibited due to steric hindrance when the fluorescent protein is fused to a target protein; that two fluorescent proteins may probably generate improper signals when they are cleaved with protease in cells; that because pH-independent fluorescence properties of the two fluorescent proteins differ from each other in terms of quenching properties caused by the folding speed or photobleaching in cells, the value of the ratio may probably vary depending on experimental conditions; that because changes in the ratio depend only on fluorescence changes of the super ecliptic pHluorin, significant changes cannot be observed; and the like.

SUMMARY OF THE INVENTION

Under the above circumstances, development of a simple and accurate method of autophagy measurement has been awaited.

The present inventors have now found a method that enables more accurate measurement of the activity of the autophagy that is the system in cells for degrading cytoplasmic materials such as proteins or organelles. More specifically, the present inventors have now found a novel method for measuring autophagy in cells, characterized by the use of a single fluorescent protein, which is resistant to degrading activities and which changes spectra depending on pH changes, as a probe, while utilizing the fact that autophagy is a reaction that the cytoplasmic materials are incorporated into the lysosome or vacuole having an acidic pH from the cytoplasm having a neutral pH. Specifically, the activity of autophagy in cells can be more accurately measured by using, as a probe reagent, a single fluorescent protein having spectra that change the fluorescence intensities in opposite directions between an acidic condition and a neutral condition.

Accordingly, this invention is summarized as follows.

(1) A method for measuring autophagy in a cell in vitro, comprising using a single fluorescent protein, as a probe reagent, to measure a change in fluorescence properties of a fluorescent probe reagent depending on pH changes associated with autophagy, thereby determining the presence or activity of autophagy, wherein the single fluorescent protein is resistant to degrading enzyme activities in the lysosome or vacuole of the cell, the single fluorescent protein is not denatured or inactivated under acidic to neutral pH environments, and the single fluorescent protein is capable of changing excitation spectra or fluorescence spectra when located under the environments of acidic region and neutral region, and wherein the change in fluorescence properties is measured by a dual wavelength excitation/single wavelength fluorescence method or a single wavelength excitation/dual wavelength fluorescence method and the fluorescence intensities are measured at two different excitation wavelengths or two different fluorescence wavelengths to determine a ratio of the fluorescence intensities.

(2) The method according to (1) above, wherein the presence or activity of autophagy is measured as the presence or amount of the probe reagent transported into the lysosome or vacuole in the cell.

(3) The method according to (1) or (2) above, wherein the acidic to neutral environment is of at least pH 4-8.

(4) The method according to any one of (1)-(3) above, wherein the fluorescent protein is a *Montipola* sp.-derived fluorescent protein or a variant thereof having equivalent fluorescence properties.

(5) The method according to any one of (1)-(4) above, wherein the fluorescent protein is present in the cell in the form of a conjugate thereof bound to a target endogenous protein optionally via a linker.

(6) The method according to (5) above, wherein the endogenous protein is a disease-associated protein.

(7) The method according to any one of (1)-(4) above, wherein the fluorescent protein is present in the cell in the form of a conjugate of the protein with a localization signal sequence for selectively transporting the protein to an organelle.

(8) The method according to any one of (1)-(7) above, wherein the fluorescent protein or conjugate is introduced into the cell in the form of an expression vector comprising DNA encoding the fluorescent protein or conjugate.

(9) A method for screening for a therapeutic agent for a disease caused by autophagy anomalies, comprising introducing a single fluorescent protein-containing probe reagent and a candidate agent into a cell associated with the disease, measuring an autophagy activity of the cell by the method according to any one of (1)-(8) above, and determining that, when the activity increases compared with that of a control, the candidate agent has a therapeutic effect, wherein the single fluorescent protein is resistant to degrading enzyme activities in the lysosome or vacuole of the cell, the single fluorescent protein is not denatured or inactivated under acidic to neutral pH environments, and the single fluorescent protein is capable of changing excitation spectra or fluorescence spectra when located under the environments of acidic region and neutral region.

(10) The method according to (9) above, wherein the disease is a neurodegenerative disease.

According to this invention, autophagy activity can be detected as greater changes in the fluorescence intensity ratio using, as a probe reagent, a single fluorescent protein having potent resistance to degradation and changing the fluorescence intensities in opposite directions between the acidic and neutral conditions, compared with the use of two conventional fluorescent proteins in combination. This enables more accurate identification of small differences in activity levels. Since measurement problems caused by different properties of two fluorescent proteins, such as folding speeds or quenching speeds, are dissolved, more quantitative measurement of autophagy becomes possible.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 1A shows the excitation spectra of mKeima (the *Montipola* sp.-derived monomeric fluorescent protein), the fluorescence spectra of the same, and pH dependency of their spectra. FIG. 1B shows pH-dependent changes in the excitation peak ratio of mKeima (586 nm/440 nm). FIG. 1C shows the excitation peak at pH 7.0 (cytoplasmic pH) and 4.0 (lysosomal pH) extracted from FIG. 1A, and it exhibits pH-dependent changes in the excitation peak.

FIGS. 2A, 2B, and 2C each show a fluorescent image obtained 24 hours after transfection of mKeima into MEF cells. Specifically, FIG. 2 shows a fluorescent image excited through a 438/24 filter (A), a fluorescent image excited through a 550DF30 filter (B), and an image of the B/A ratio (C). In the figure, a signal emitted by mKeima transported to the acidic lysosome via autophagy is observed. FIG. 2D shows a ratio value of the mKeima signals from the cytoplasm or lysosome (550 nm/438 nm).

FIGS. 3A, 3B, and 3C each show the induction of mitophagy by treating 2×COX8 mKeima-expressing MEF cells with 2 mM FCCP+1 mg/ml Oligomycin. Specifically, FIG. 3 shows a fluorescent image excited through a 438/24 filter (A), a fluorescent image excited through a 550DF30 filter (B), and an image of the B/A ratio (C). FIG. 3D shows a ratio value of the mKeima signals from the mitochondria or lysosome (550 nm/438 nm).

EMBODIMENTS FOR CARRYING OUT THE INVENTION

Figure 1:
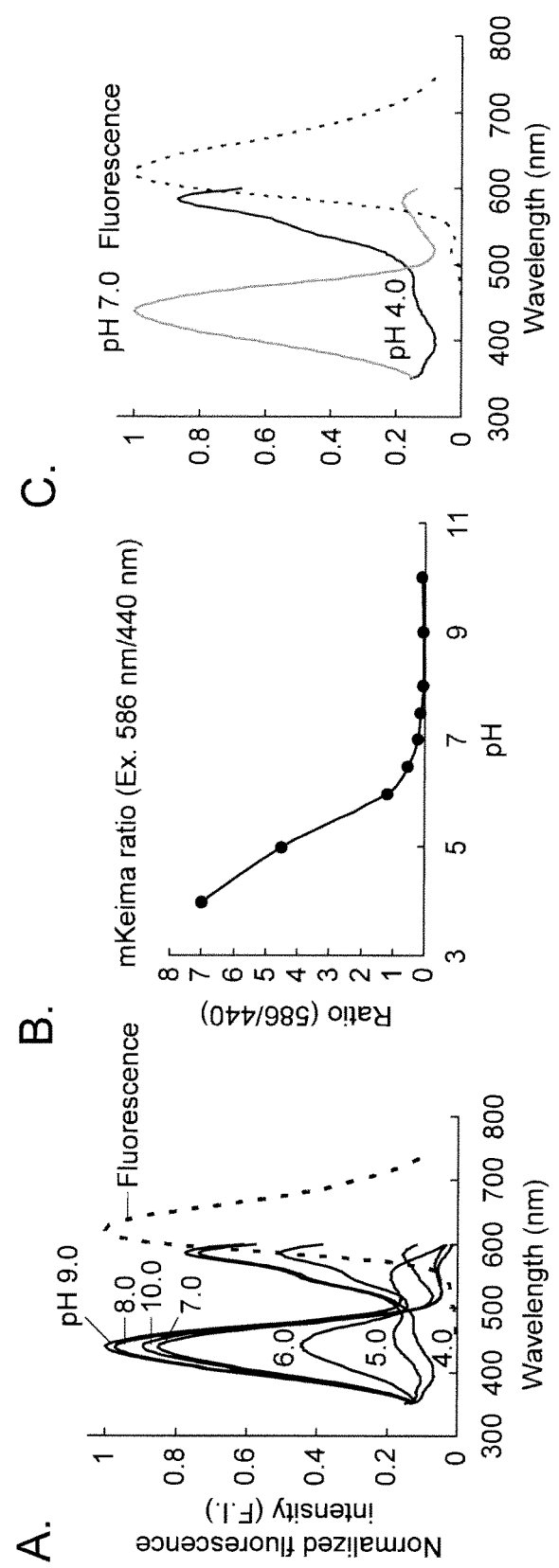
FIG. 1 shows changes in the excitation spectra of mKeima depending on pH changes.

Hereafter, this invention is described in more detail.

This invention provides a method for measuring autophagy in cells, comprising using a single fluorescent protein, which has resistance to degrading enzyme activities in the lysosomes or vacuoles of the cells, which is not denatured or deactivated under acidic to neutral pH environments, and which is capable of changing the excitation or fluorescence spectra under the acidic to neutral environments, as a probe reagent, and measuring changes in fluorescence properties of a fluorescent probe reagent associated with autophagy and depending on changes in pH, thereby determining the presence or activity of autophagy.

<Autophagy>

As described in the "Background Art" above, autophagy is a mechanism of a cell for degrading its own cytoplasmic materials, such as proteins or organelles (e.g., mitochondria or endoplasmic reticulum), and autophagy is classified into three types based on its mechanisms; i.e., macroautophagy, microautophagy, and chaperone-mediated autophagy. The method of this invention enables accurate measurement of the total autophagy activities occurring in cells.

The term "autophagy activity" used herein refers to the capacity for clearance in cells. When autophagy activity is higher, the clearance is regarded as functioning in living cells. When autophagy normally takes place, cellular homeostasis is considered to be maintained.

Macroautophagy is a degradation pathway that functions as follows. When cells receive a stress, such as nutrient starvation, excessive protein production, or accumulation of abnormal proteins, cytoplasmic materials, such as proteins or organelles, and phospholipids accumulate in the cytoplasm, and the autophagosome is formed. In the case of animal cells, the autophagosome undergoes membrane fusion with the intracellular lysosome to form an autolysosome. In the case of yeast or plant cells, the autophagosome undergoes membrane fusion with vacuoles, and cytoplasmic materials are consequently degraded by proteolytic enzymes existing in lysosomes or vacuoles.

Microautophagy is a degradation pathway that functions as follows. Cytoplasmic materials, such as excessively produced proteins or abnormal proteins, are directly incorporated into lysosomes or vacuoles without undergoing membrane fusion and degraded therein.

Chaperone-mediated autophagy is a degradation pathway that functions as follows. Chaperone binds to cytoplasmic materials, such as excessively produced proteins or abnormal proteins, and incorporates the cytoplasmic materials into lysosomes or vacuoles to degrade the cytoplasmic materials.

Recent studies have demonstrated that autophagy is related to various vital phenomena, such as quality control of proteins or organelles, bacterial infection, antigen presentation, cell death or apoptosis, canceration, and embryogenesis. In addition, autophagy is considered to be associated with degradation or elimination of abnormal proteins that accumulate and aggregate in cells. Further, involvement thereof with neurodegenerative diseases such as the Huntington's disease and the Alzheimer's disease, which are considered to be caused by cell death due to accumulation of such abnormal proteins, has been suggested. Accurate measurement of autophagy activity may lead to elucidation of causes of such diseases or development of therapeutic methods for such diseases.

<Fluorescent Protein>

The method of this invention is characterized by the use of a single fluorescent protein as a probe reagent. This fluorescent protein has properties as described below: i.e., (i) it is resistant to degrading enzyme activities in the lysosome or vacuole of a cell; (ii) it is not denatured or deactivated in acidic to neutral pH environments in a cell; and (iii) it is capable of changing the excitation or fluorescence spectra under the acidic to neutral environments in a cell.

The property (i) is characterized in that a fluorescent protein is resistant to degrading enzyme activities. This is because the method of the invention is intended to measure autophagy and, if the probe reagent used for such measurement is degraded in the lysosome or vacuole, accurate measurement cannot be realized.

The property (ii) is characterized in that a fluorescent protein should not be denatured or deactivated in the intracellular environments of neutral to acidic conditions. This is because, while the cytoplasm has a pH of a neutral region, the lysosome or vacuole has a pH of an acidic region, and the probe reagent used in the invention is placed in the intracellular environments of neutral to acidic conditions.

The property (iii) is characterized in that the fluorescent protein has spectra that change fluorescence intensities in opposite directions between the acidic region and the neutral region when the probe reagent is placed under the acidic and neutral environments. As seen in FIG. 1A, the isosbestic or isofluorescent point exhibiting substantially constant fluorescence intensity is present at about 500 nm without depending on pH changes, and the fluorescence intensities change in opposite directions before and after said wavelength depending on pH changes (FIG. 1C). Based on such spectral waveforms, the fluorescence intensities can be measured at two adequate wavelengths positioning on both sides of the isosbestic point or the isofluorescent point, whereby the measurement of fluorescence by the ratiometric method becomes possible. In addition, because fluorescence intensities are changed in opposite directions at two wavelengths, significant or large changes in the ratio can be obtained.

Examples of fluorescent proteins having such properties include, but are not limited to, the *Montipora* sp-derived fluorescent protein (Keima), such as monomeric Keima (mKeima) or dimeric Keima (dKeima), and varianst thereof having equivalent fluorescent properties to those of Keima, such as dKeima-Red™ (Amalgaam, MBL; Kogure, T. et al., 2006, Nat. Biotechnol. 24: 577-581).

The term "equivalent fluorescent properties" used herein refers to the property (iii) above, in particular; however, the variants that can be used in this invention should also have the properties (i) and (ii).

As described in Example 1 below, for example, the excitation peaks of mKeima are 586 nm at pH 4.0 and 440 nm at pH 7.0 and have an isosbestic point at about 500 nm, and the fluorescence intensities change in opposite directions before and after said wavelength depending on pH values. On the other hand, the fluorescence wavelength is 620 nm at the peak, which remains substantially constant between pH 4 and pH 10.

In the case of dKeima-Red, the maximal excitation wavelength is 440 nm, the maximal fluorescent wavelength is 616 nm, and the isosbestic point thereof is present around 550 nm.

Mutation such as amino acid substitution is often introduced into a fluorescent protein in order to impart fluorescent properties different from those of a naturally-occurring protein. Such substitution is conservative or nonconservative amino acid substitution and is a substitution between amino acids having the same or different chemical or physical properties, such as electric, structural, or hydrophobic/polar properties. Examples of hydrophobic amino acids include Gly, Ile, Val, Leu, Ala, Met, and Pro. Examples of polar amino acids include Asn, Gln, Thr, Ser, Tyr, and Cys. Examples of acidic amino acids include Asp and Glu. Examples of basic amino acids include Arg, Lys, and His. Examples of aromatic amino acids include Phe, Tyr, Trp, and His. Substitution can be carried out via site-directed mutagenesis, which may be carried out in combination with PCR (Sambrook et al., Molecular Cloning, Vol. 2, Current Protocols in Molecular Biology, 1989, Cold Spring Harbor Laboratory Press; Mark, D. F. et al., Proc. Natl. Acad. Sci., U.S.A., 81: 5662-5666, 1984) or with the use of a commercially available mutagenesis kit (e.g., Mutan-super Express Km Kit (Takara)).

It is preferable to cause structural changes such that a protein has fluorescence and enhanced stability in order to change spectral properties. To this end, nonconservative amino acid substitution is preferable. In any case, the fluorescent protein used in this invention should have properties (i), (ii), and (iii) above, and a fluorescent protein having spectral properties as shown in FIG. 1A can be selected from among various novel and known fluorescent proteins by conducting experiments exemplified in the <Excitation spectra of mKeima> of Example 1.

The fluorescent protein used in this invention may be any of a protein purified from a naturally occurring protein, a recombinant protein, or a protein chemically synthesized, i.e. obtained by peptide synthesis. A recombinant protein is preferable since relatively large quantities thereof can be produced.

A recombinant protein can be produced using conventional gene recombination techniques (e.g., Sambrook et al., Molecular Cloning, Vol. 2, Current Protocols in Molecular Biology, 1989, Cold Spring Harbor Laboratory Press; and Ausubel et al., Short Protocols in Molecular Biology, Vol. 3, A compendium of Methods from Current Protocols in Molecular Biology, 1995, John Wiley & Sons).

DNA encoding a fluorescent protein is cloned from an organism cell in which the protein is expressed. When the primary structure of such DNA is known, specifically, primers are synthesized based on a partial sequence of the DNA, a polymerase chain reaction (PCR) is carried out using a cDNA library of the cell as a template to amplify a DNA of interest, which is then inserted into an adequate vector (e.g., plasmid, phage, or cosmid). Thus, cloning can be carried out.

A fluorescent protein can be produced by gene recombination techniques using procaryotes, such as Escherichia (e.g., *E. coli*), Bacillus (e.g., *Bacillus subtilis*), Brevibacillus (e.g., *Bacillus brevis*), and *Pseudomonas*, and plasmid vectors suitable for such cells.

Examples of *E. coli* plasmids that can be used include, but are not limited to, plasmids of pBluescript series, pUC series such as pUC 18 and pUC 19, pBR series such as pBR322, pQE series such as pQE-30 and pQE-60, and pMAL series such as pMAL-C2 and pMAL-p2.

A vector can adequately comprise a primer, a replication origin, the Shine-Dalgarno (SD) sequence, a termination codon, a terminator, a poly A sequence, or a multicloning site. Since a multicloning site comprises a plurality of restriction enzyme recognition sites, it is convenient when a DNA of interest is inserted. In addition, a vector may also comprise a selection marker, such as a drug resistance gene (e.g., ampicillin resistance gene or kanamycin resistance gene), where needed. Further, a DNA encoding an His tag (any of $(His)_6$ to $(His)_{10}$) may optionally be bound to the 5'- or 3'-end of a DNA encoding a fluorescent protein of interest in order to facilitate protein purification, and it may be expressed in the form of a fusion protein.

Examples of promoters include, but are not limited to, lac promoter, trp promoter, $\lambda P_L$ promoter, $\lambda P_R$ promoter, tac promoter, and glycolytic enzyme promoters.

Introducing a vector into cells (i.e., transformation) can be conducted by techniques such as the calcium phosphate, lipofection and electroporation methods.

A recombinant protein expressed in cultured cells can be recovered and purified from the cells or from extracellular fluid (when a signal peptide is used) by techniques, such as cell wall destruction, ammonium sulfate, ethanol precipitation, acid extraction, anion or cation exchange chromatography, hydrophobic interaction chromatography, affinity chromatography, and HPLC.

In this invention, the fluorescent protein or a vector comprising DNA encoding the same is used in order to measure cellular autophagy (the activity or presence thereof). Since the cells used herein are eucaryocytes (e.g., fungal cells, such as yeast, filamentous fungi, or basidiomycetes, plant cells, insect cells, or animal cells such as mammalian cells), in particular, vectors suitable for such cells are used (e.g., plasmid, phage, cosmid, or virus vectors).

Examples of vectors suitable for yeast cells include pG-1, YEp13, YCp50, pGBT9, pGAD424, and pACT2 vectors (manufactured by Clontech).

Examples of vectors suitable for plant cells include pBI and T-DNA vectors.

Examples of vectors suitable for animal cells include pRc/RSV, pEF6/Myc-His, pRc/CMV (e.g., Invitrogen), bovine papilloma virus plasmid (pBPV) (Amersham Pharmacia Biotech), EB virus plasmid (pCEP4) (Invitrogen), and insect virus vectors, such as baculovirus vectors.

A vector can optionally comprise a primer, an enhancer, a replication origin, a ribosome binding sequence, a termination codon, a terminator, a poly A sequence, or a multicloning site. A vector can comprise a selection marker for a drug resistance gene (e.g., ampicillin resistance gene, kanamycin resistance gene, or hygromycin resistance gene) or an auxotrophic complementary gene (e.g., HIS3, LEU2, LYS2, TRP1, or URA3), where needed. In addition, a DNA encoding an His tag (e.g., any of $(His)_6$ to $(His)_{10}$) may optionally be bound to the 5'- or 3'-end of a DNA encoding a fluorescent protein of interest in order to facilitate protein purification, and it may be expressed in the form of a fusion protein.

Examples of promoters include, but are not limited to, ADH1, ubiquitin, cauliflower mosaic virus, Rous sarcoma virus (RSV), cytomegalovirus (CMV), early or late simian virus (SV40), and mouse mammary tumor virus (MMTV) promoters.

Introducing a vector into cells (i.e., transformation or transfection) can be conducted by techniques, such as calcium phosphate, DEAE dextran, lipofection, electroporation, microinjection, liposomes, Agrobacterium, gene gun, viral infection, and spheroplast or protoplast methods.

When the fluorescent protein is directly introduced into a cell, alternatively, the fluorescent protein may be bound to a membrane-permeable peptide or encapsulated into a liposome, in order to introduce the resulting product into a cell.

The fluorescent protein used in this invention may be introduced into a cell alone or in the form of a conjugate with an endogenous protein, polypeptide, or peptide associated with autophagy or other functional protein, polypeptide, or peptide (i.e., a conjugate or fusion protein).

Examples of the endogenous protein, polypeptide, or peptide include every type of protein, polypeptide, or peptide associated with autophagy against a disease, nutrient starvation, bacterial infection, immune response or antigen presentation, cell death or apoptosis, canceration, or the like. Examples of disease include, but are not limited to, neurodegenerative diseases, such as Huntington's disease, Alzheimer's disease, and Parkinson's disease, cancers, cardiac failure, and diabetes. The endogenous protein is associated with causes of such diseases (i.e., a disease-associated protein). Examples of such disease-associated proteins include amyloid precursor protein, polyglutamine, α-synuclein, and parkin.

Examples of the other functional proteins, polypeptides, or peptides include a localization signal sequence capable of selectively transferring a protein to a given organelle such as the mitochondria or endoplasmic reticulum (e.g., a mitochondrial localization signal peptide or a chloroplast localization signal peptide), a membrane-permeable peptide capable of introducing a protein into cells (e.g., polyarginine or Tat peptide), and an antibody capable of specifically binding to the endogenous protein (e.g., a monoclonal, single cahin antibody, or synthetic antibody) or a fragment thereof.

The amino acid and nucleotide sequences for the proteins, polypeptides, or peptides above are available from literature or DNA databases, such as DDBJ/EMBL/GenBank (NCBI, U.S.A.).

The conjugate can be prepared by binding a protein to a protein, a protein to a polypeptide, or a protein to a peptide via a linker if required. The linker is a peptide comprising approximately 2 to 50 amino acid residues, and any peptide can be used as a linker, as long as it does not disturb cellular functions and does not affect properties, conformation and the like of the fluorescent protein and the endogenous proteins.

DNA encoding the conjugate described above is synthesized, and then inserted into the vector, introduced into cells, and expressed in the cells. A technique thereof is as described above.

<Measurement of Autophagy>

According to the method of this invention, autophagy activity in a cell is determined by measuring pH-dependent changes in spectral properties of a single fluorescent protein serving as a probe reagent.

When measuring autophagy according to the method of this invention, a fluorescent protein can be used alone or in the form of a conjugate in a cell. Examples of using the fluorescent protein include the following.

(a) Since autophagy takes place at an undesignated site of the cytoplasm, the fluorescent protein is expressed in the cytoplasm, and the total amount of autophagy is measured based on changes in fluorescence when the fluorescent protein is transferred into the lysosome.

(b) When measurement of autophagy of an endogenous protein of interst such as a disease-associated protein (i.e., an autophagy-associated protein) is intended, the protein of interest is fused to the fluorescent protein, expressed, and measured for fluorescence.

(c) When measurement of autophagy of an organelle of interest (e.g., mitochondria) is intended, a localization signal sequence used for selectively localizing a fluorescent protein or conjugate is fused to the fluorescent protein, expressed, and measured for fluorescence.

Since there were no probe reagents sufficient for measurement of the total amount of autophagy in the past, it was necessary to label the autophagy-associated protein in order to measure the autophagy based on the pharmacokinetics of the protein. In contrast, the use of a fluorescent protein with properties as used in this invention eliminates such necessity, and autophagy can be measured while focusing on a protein or organelle of interest.

Furthermore, in the single expression of a fluorescent in a cell, an event such as a particular disease is not a direct subject for measurement, and instead, the ability of the cell to activate autophagy is measured. This enables detection of an ability of the cell to activate the metabolism, whereby a likelihood of being afflicted with a disease or an indicator of aging can be determined based thereon.

In this invention, any types of eucaryocytes can be used. Specific examples of such cells include, but are not limited to, fungal cells such as yeast cells, plant cells, and animal cells (e.g., invertebrate cells, vertebrate cell, warm-blooded animal cells, mammalian cells, and human cells).

According to the method of this invention, a single fluorescent protein, which is resistant to degrading enzyme activities in the lysosome or vacuole of a cell, which is not denatured or deactivated under acidic to neutral environments between pH 4 and pH 8 at least, and which significantly changes the excitation or fluorescence spectra when the fluorescent protein is placed in such acidic to neutral environments, is used as a fluorescent probe reagent. Such spectra has an isosbestic or isofluorescent point with substantially constant fluorescence intensity independent of pH changes, and has a property of changing fluorescence intensities in opposite directions before and after the wavelength of the isosbestic or isofluorescent point depending on pH changes. Because of such spectral properties, fluorescence intensities are measured at two adequate wavelengths positioning on both sides of the isosbestic or isofluorescent point, and this enables fluorescence measurement by the ratiometric method. Thus, because fluorescence intensities change in opposite directions at two wavelengths, significant or large changes can be attained in the fluorescence intensity ratio.

By the ratiometric method, pH-independent changes in fluorescence intensities, such as differences in probe reagent distribution in a cell, variations in excitation lights, or photobleaching of fluorescence, can be cancelled, and more quantitative measurement can be performed. Since measurement is carried out with the use of a single fluorescent protein, this technique is free of problems caused by the use of two fluorescent proteins as described above. Because of such properties, transfer of a probe reagent to the lysosome or vacuole, i.e. autophagy activity, can be clearly and accurately measured. With the use of a fluorescent protein, which is highly resistant to degrading enzymes, the total amount of autophagy activities that have occurred within an arbitrary duration can be measured.

The probe reagent can be expressed in a cell by introducing a gene, DNA, or RNA encoding the amino acid sequence of the probe reagent into the cell, or alternatively the probe reagent can be directly introduced into a cell, for use in measurement of autophagy in a cell. A probe reagent or a gene, DNA, or RNA encoding the same can be introduced into a cell by techniques, such as the calcium phosphate, DEAE dextran, lipofection, electroporation, microinjection, liposomes, ligation to a membrane-permeable peptide, Agrobacterium, virus infection, spheroplast, and protoplast methods, as described above. In addition to a technique for transiently expressing a probe reagent in a cell, the gene or DNA for the probe reagent may be retained in a cell to prepare a cell that stably expresses the probe reagent, and the obtained cell may be used for the measurement. To this end, a strong promoter or autonomously replicating vector can be used, for example.

The fluorescent probe reagent may be fused to a certain protein and expressed in a cell. Alternatively, a localization signal sequence used for selectively localizing the probe reagent in a certain organelle may be added to express it. Thus, autophagy for a certain protein or organelle can be measured.

Measurement of fluorescence can be carried out by the dual wavelength excitation/single wavelength fluorescence method in which fluorescence intensities are measured at two different excitation wavelengths at which a fluorescent protein serving as the probe reagent significantly changes the excitation spectra depending on pH changes but changes in the fluorescence spectra are small, and thus the ratio of the fluorescence intensities is determined. When the fluorescence spectra are significantly changed depending on pH changes but changes in the excitation spectra are small, however, fluorescence intensities can be measured by the single wavelength excitation/dual wavelength fluorescence method in which fluorescence intensities are measured at two different fluorescent wavelengths, and thus the ratio of the fluorescence intensities is determined.

Autophagy can be measured in accordance with the method specifically described in Example 1. For example, cells are seeded on a culture dish, and culture is conducted in a conventional culture medium for yeast, plant cells, or animal cells overnight. A fluorescent protein or conjugate (i.e., the probe reagent) or a vector comprising DNA encoding the same is introduced into a cell by the method described above. After culture is conducted for approximately 6 hours, the medium is exchanged with a fresh medium, culture is conducted for an additional 24 hours, and analysis using the fluorescence microscopic imaging system is then carried out. In such a case, autophagy is measured for the presence or amount of the probe reagent that has transferred to the lysosome or vacuole in a cell.

When measurement is carried out at a single cell level, a microscopic imaging system comprising a fluorescence microscope to which a detector such as a cooled CCD camera has been connected can be used as an apparatus for measurement of fluorescence. If an analyzer has functions of time-lapse imaging, autophagy that occurs in a cell can be visualized in real time. In the case of the dual wavelength excitation/single wavelength fluorescence method, a wavelength switching apparatus is combined with a light source for excitation of a microscope, thereby enabling selection of any two wavelengths. Examples of the usable wavelength switching appartus include a filter switching apparatus and a monochrometer. On the other hand, in the case of the single wavelength excitation/dual wavelength fluorescence method, a filter switching apparatus and a dual wavelength spectrophotometer for imaging are connected in front of a detector. In addition, a laser scanning confocal microscope, a multiphoton excitation microscope, or the like can be used as an imaging apparatus for the microscope. When measurement at a single cell level is not necessary, measurement can be carried out by using an apparatus for fluorometry, such as a general fluorospectrophotometer or flow cytometory.

<Method for Screening For Therapeutic Agent>

This invention further provides a method for screening for a therapeutic agent for a disease caused by autophagy anomalies, comprising introducing a single fluorescent protein-containing probe reagent and a candidate agent into a cell associated with the disease, measuring an autophagy activity of the cell by the method for measuring the autophagy activity as described above, and determining that, when the activity increases compared with that of a control, the candidate agent has a therapeutic effect, wherein the single fluorescent protein is resistant to degrading enzyme activities in the lysosome or vacuole of the cell and is not denatured or inactivated under acidic to neutral pH environments but is capable of changing excitation spectra or fluorescence spectra when located under the environments of acidic region and neutral region.

The screening method of this invention comprises providing a cell associated with a disease caused by autophagy anomalies (including a cell system), introducing a probe reagent comprising the fluorescent protein (e.g., a probe reagent to which a disease-causing protein has been fused or a probe reagent to which an antibody having binding affinity to the disease-causing protein or a fragment thereof has been fused) and a drug candidate into the cell, and measuring the autophagy activity by the measurement methods as described above.

The probe reagent may be coded into a vector. In such a case, the probe reagent is expressed in a cell to serve as a protein probe reagent. Alternatively, when a cell membrane-permeable peptide is fused to the probe reagent, the probe reagent can be directly introduced into the cell.

As described above, autophagy is known to be associated with: for example, neurodegenerative diseases such as Huntington's disease, Alzheimer's disease, or Parkinson's disease; diseases such as cancers, cardiac failure, or diabetes; nutrient starvation; bacterial infections; immune response or antigen presentation; and (programmed) cell death (Tamotsu Yoshimori (ed.), "Shikkan ni taikousuru autophagy (Autophagy against disease)," Jikken Igaku (Experimental Medicine) Vol. 27, No. 18, 2009, Yodosha Co., Ltd., Japan). Such diseases can become the targets of the method of this invention. The method of this invention is particularly useful for screening for therapeutic agents for neurodegenerative diseases, such as Huntington's disease, Alzheimer's disease, and Parkinson's disease, and cancers.

According to the method of this invention, when autophagy activity is enhanced compared with that of a control (i.e., an activity determined using a cell containing no drug candidate), a drug candidate is determined to have a therapeutic effect.

Examples of drug candidates include, but are not limited to, low molecular weight compounds (or small molecules), high molecular weight compounds, natural compounds, inorganic compounds, organic compounds, proteins (or polypeptides), peptides, amino acids, carbohydrates (or saccharides), oligosaccharides, lipids (including phospholipids), nucleic acids (including artificial nucleic acids), oligonucleotides, siRNA, shRNA, miRNA, and nucleosides.

EXAMPLES

Hereafter, this invention will be described in more detail with reference to the examples, although the technical scope of this invention is not limited to the examples.

Example 1

An example of autophagy measurement with the use of a *Montipora* sp-derived fluorescent protein (a monomeric protein, mKeima) as a fluorescent probe reagent is described below.

<Excitation Spectra of mKeima> mKeima was purified in the following manner, and pH-dependent spectral properties were studied.

pRSET$_B$ (Invitrogen) into which mKeima cDNA had been inserted (note: cDNA cloning is described in Kogure, T. et al., 2006, Nat. Biotechnol., 24: 577-581) was introduced into the JM109 (DE3) competent cells. The competent cells were applied to an LA plate and cultured at 37° C. overnight. The resulting colonies were transferred to 100 ml LA medium and then subjected to shake culture at 18° C. for 72 hours. The colonies were lysed by means of freezing and thawing, and then the mKeima-containing supernatant obtained after centrifugation was applied to a nickel column (Qiagen) and subjected to elution through the column. In order to remove imidazole used during the above procedure, mKeima was finally purified by gel filtration using Sephadex™ G-25 (Pharmacia).

The above-purified mKeima was diluted with any of buffers (pH 4-10) to a concentration of 2 µg/ml. A buffer with pH 4.0-5.0 is 50 mM acetate buffer comprising 30 mM KCl and 120 mM sodium gluconate, a buffer with pH 6.0 is $Na_2HPO_4$-$NaH_2PO_4$ buffer, a buffer with pH of 7.0-8.0 is HEPES buffer, and a buffer with pH 9.0-10.0 is glycine buffer. The excitation spectra of mKeima were measured at the excitation wavelength of 350 to 600 nm and the fluorescence wavelength of 620 nm with the use of a fluorospectrophotometer (SPEX Fluorolog-3, Horiba Ltd., Japan).

FIG. 1 shows the spectra standardized by designating the measured maximal fluorescence intensity as 1. The obtained results demonstrate that the excitation peaks of mKeima are 586 nm at pH 4.0 and 440 nm at pH 7.0, the isosbestic point of their spectra is present at approximately 500 nm, and fluorescence intensities change in opposite directions before and after this wavelength (i.e., 500 nm) depending on pH values. The fluorescence wavelength has the peak at 620 nm, which is substantially constant between pH 4 and pH 10. Since pKa is 6.5, which is in the middle of the lysosome pH and the cytoplasm pH, this fluorescent protein was found to have adequate properties as a probe reagent used for autophagy measurement.

<Detection of Autophagy in Cell>

The pEF6/Myc-His plasmid (Invitrogen) into which mKeima cDNA described above had been inserted was transfected into the mouse embryonic fibroblast (MEF) cells as an example, and the detection and visualization of autophagy were performed.

The MEF cells were seeded in glass bottom dishes (diameter: 35 mm) and cultured in a DMEM medium containing 5% fetal bovine serum overnight. Plasmid DNA (1µl g) was mixed with 100µl Opti-MEM medium. Also, Lipofectamine™ 2000 (1.5µl, Gibco BRL) was mixed with 100µl of Opti-MEM medium. These mixtures were allowed to stand at room temperature for 5 minutes, mixed with each other, and then allowed to stand for additional 15 minutes. The obtained mixture was added to the dish in which cells had been cultured, and after 6-hr culture, the medium was exchanged with a fresh medium in order to subject to additional 24-hr culture, and the obtained cells were analyzed using the fluorescence microscopy imaging system. Imaging was carried out with the use of the iXon EM+ camera (Andor Technology), the UPlanSApo60x, oil objective lens (Olympus Corporation, Japan), a 438 nm bandpass filter with a 24 nm half power bandwidth (Semlock) and a 550 nm bandpass filter with a 30 nm half power bandwidth (Omega) as excitation filters, and a 610 nm longpass filter (Omega) and a 590 nm dichroic mirror (Omega) as fluorescence filters. Images were obtained and analyzed with the use of MetaMorph (Universal Imaging Corporation).

Figure 2:
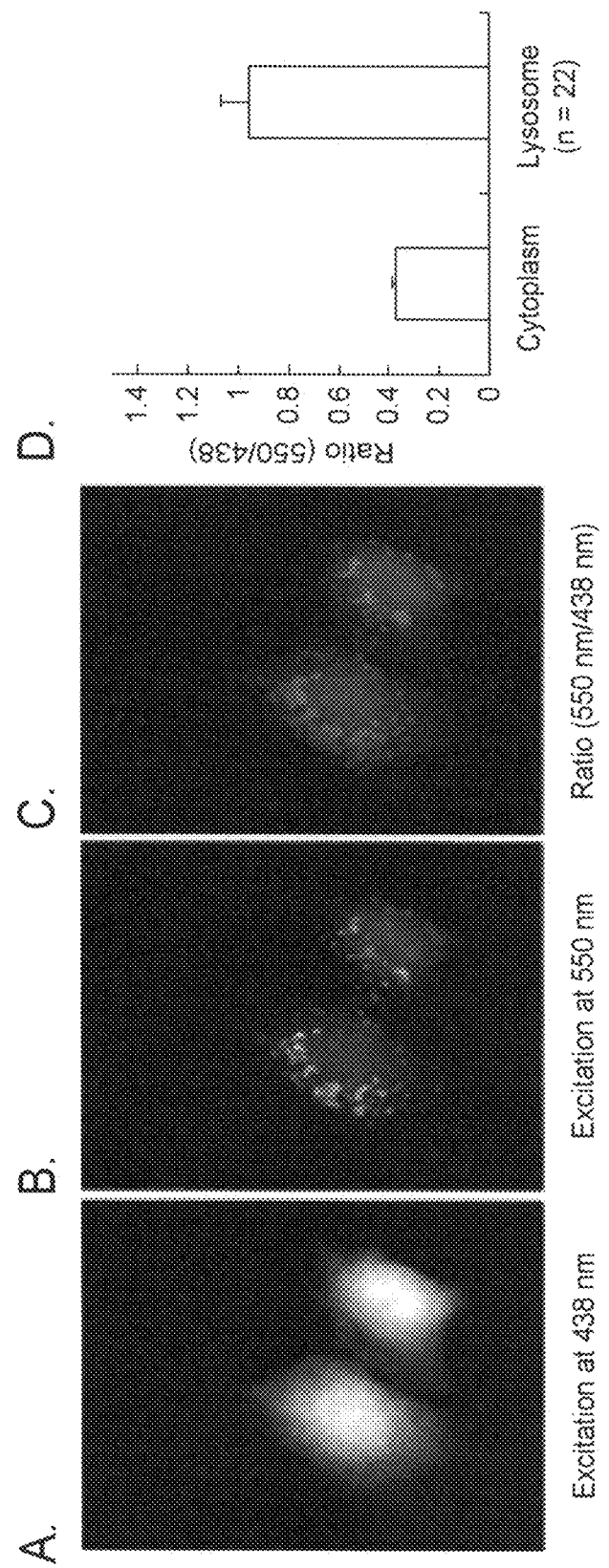
FIG. 2 shows an example of autophagy detection in MEF cells.

FIG. 2 shows the results. Many vesicles emitting potent fluorescence at the excitation wavelength of 550 nm were observed in cells to which mKeima DNA were added after the cells had been cultured for 24 hours. The ratio of the emitted fluorescence intensities at 550 nm/438 nm was determined, a high value was obtained in the vesicles, and a pH in that region was found to be in an acidic region. The distribution of the vesicles was compared with distribution of the fluorescence of Alexa488-dextran, which is a fluorescent pigment selectively staining lysosomes. As a result, from the fact that their localizing patterns were overlapped with each other, the vesicles were confirmed to be lysosomes. These results demonstrate that autophagy occurring in the MEF cells is detected as changes in fluorescence properties caused by transportation and accumulation of mKeima in the lysosomes.

<Detection of Mitophagy in Cell>

Mitophagy (which refers to mitochondrial autophagy) was detected by selectively expressing mKeima in the mitochondria of the MEF cell as an example and measuring the fluorescence of mKeima.

The MEF cells were seeded in glass bottom dishes (diameter: 35 mm) and cultured in a DMEM medium containing 5% fetal bovine serum overnight. Plasmid DNAs of the ecdysone-inducible vector pIND (SP1) into which 2×COX8mKeima cDNA had been inserted (Invitrogen), the pVgRXR vector which expresses the ecdysone receptor RXR (Invitrogen), and a vector, EGFP-Parkin pEF6/Myc-His, which expresses the mitophagy promoting factor Parkin (0.5 µg each, 1.5 µg in total) were mixed with 100 µOpti-MEM medium. Also, 1.5 µl Lipofectamine™ 2000 was mixed with 100 µOpti-MEM medium. These mixtures were allowed to stand at room temperature for 5 minutes, mixed with each other, and then allowed to stand for an additional 15 minutes. The obtained mixture was added to the dish in which cells had been cultured, and after 6-hr culture, the medium was exchanged with a fresh medium containing 2 µM ponasterone A (Invitrogen) to induce 2×COX8mKeima expression. After additional 24-hr culture, the induction of expression of 2×COX8mKeima remaining in the cytoplasm was terminated, the medium was exchanged with a medium from which ponasterone A had been removed in order to completely target mitochondria, culture was conducted overnight, and the obtained cells were then analyzed by the fluorescence microscopy imaging system. Mitophagy was induced with the addition of 2 µM FCCP (Sigma) and 1 µg/ml Oligomycin (Sigma). The system used for the autophagy detection described above was used for the imaging.

Figure 3:
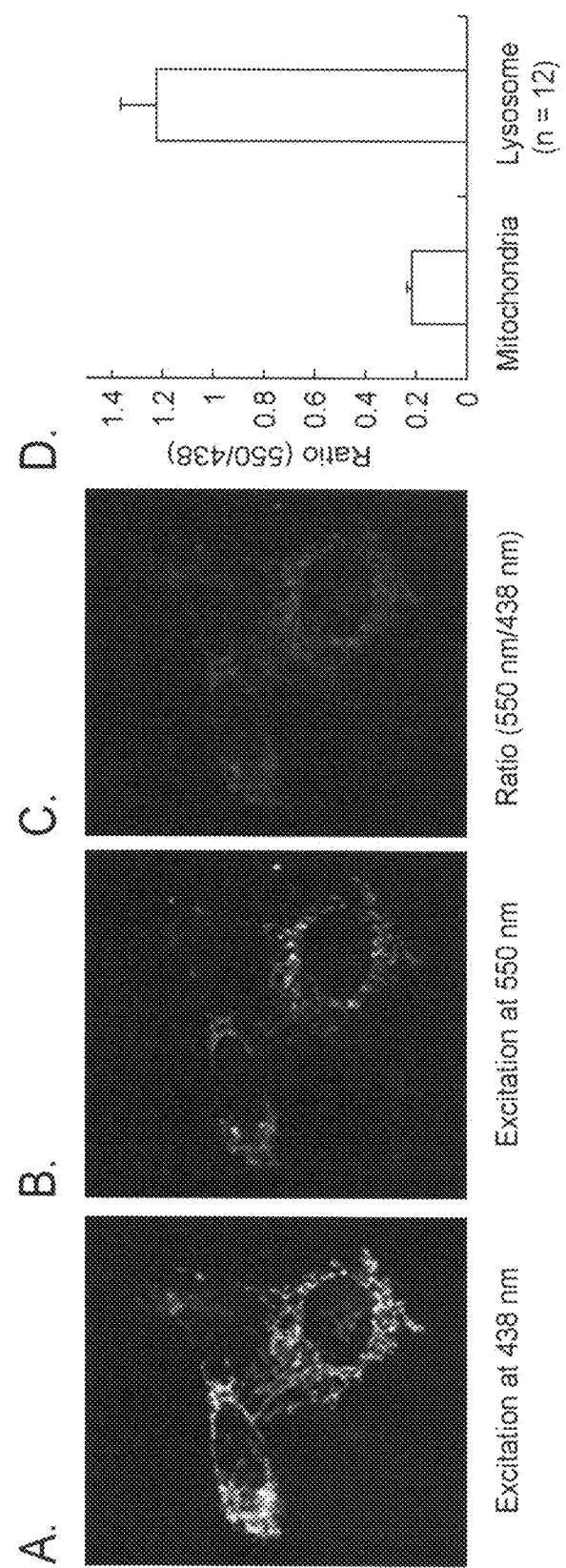
FIG. 3 shows an example of mitophagy detection in MEF cells.

FIG. 3 shows the results. At the time of 24 hours after mitophagy induction, some mitochondria in the cells were observed to emit potent fluorescence by excitation at 550 nm. The ratio of fluorescence intensities at 550 nm/438 nm was determined, and a high ratio value was obtained in mitochondria, suggesting that the pH in that region was acidic. These results demonstrate that mitophagy occurring in the MEF cells is detected as changes in fluorescence properties caused by transportation and accumulation of mKeima in the lysosomes.

INDUSTRIAL APPLICABILITY

In recent years, neurodegenerative diseases, such as Alzheimer's disease, Parkinson's disease, or Huntington's disease, were found to be caused by accumulation of abnormal proteins due to insufficient autophagy in a cell. This invention is useful in the medical and industrial fields, in respect of elucidation of such diseases, development of therapeutic methods therefor, and screening of drugs used for treating such diseases.

All publications, patents, and patent applications cited herein are incorporated herein by reference in their entirety.

The invention claimed is:

1. A method for measuring autophagy in a cell in vitro, comprising:
   (1) introducing a single fluorescent protein, as a probe reagent, or a vector comprising DNA encoding the single fluorescent protein, into the cell, wherein the single fluorescent protein is a fluorescent protein Keima that is selected from the group consisting of monomeric Keima and dimeric Keima, and is pH sensitive;
   (2) measuring a change in fluorescence intensity at a first excitation wavelength of 586 nm and a second excitation wavelength of 440 nm of the single fluorescent protein depending on pH changes associated with autophagy, in the cell that is under stress, by a dual wavelength excitation/single wavelength emission fluorescence method; and
   (3) correlating a ratio of fluorescence intensity between the first and second excitation wavelengths of the single fluorescent protein at pH 4.0 and pH 7.0, respectively, with autophagy activity in the cell, and determining that autophagy occurs in the cell when the ratio of fluorescence intensity between the first and second excitation wavelengths in the cell is higher than a control ratio that is observed in the cell in the absence of autophagy.

2. The method according to claim 1, wherein the presence or activity of autophagy is measured as the presence or amount of the probe reagent transported into the lysosome or vacuole in the cell.

3. The method according to claim 1, wherein the fluorescent protein is present in the cell in the form of a conjugate thereof bound to a target endogenous protein.

4. The method according to claim 3, wherein the endogenous protein is a disease-associated protein.

5. The method according to claim 1, wherein the fluorescent protein is present in the cell in the form of a conjugate of the protein with a localization signal sequence for selectively transporting the protein to an organelle.

6. The method according to claim 1, wherein the fluorescent protein or conjugate is introduced into the cell in the form of an expression vector comprising DNA encoding the fluorescent protein or conjugate.

7. The method according to claim 1, wherein the fluorescent protein is present in the cell in the form of a conjugate thereof bound to a target endogenous protein via a linker.

8. The method according to claim 1, wherein the fluorescent protein has a constant peak wavelength for fluorescence spectra.

* * * * *